United States Patent
Kajihara et al.

(10) Patent No.: US 6,552,218 B2
(45) Date of Patent: Apr. 22, 2003

(54) PROCESS FOR PRODUCING HYDROXYALKYL (METH)ACRYLATE

(75) Inventors: Tetsuya Kajihara, Himeji (JP); Tokumasa Ishida, Himeji (JP); Yasuhiro Shingai, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/944,087

(22) Filed: Sep. 4, 2001

(65) Prior Publication Data

US 2002/0032345 A1 Mar. 14, 2002

(30) Foreign Application Priority Data

Sep. 8, 2000 (JP) ........................................ 2000-273623

(51) Int. Cl.$^7$ ............................................... C07C 67/26
(52) U.S. Cl. ..................................................... 560/209
(58) Field of Search ................................ 560/209, 218, 560/4

(56) References Cited

U.S. PATENT DOCUMENTS 3,709,928 A * 1/1973 Masayuki et al.
3,987,090 A * 10/1976 Gruber et al.
5,342,487 A    8/1994 McDade et al. ............... 203/6

FOREIGN PATENT DOCUMENTS

JP    51133227    11/1976
JP    5194321     8/1993

OTHER PUBLICATIONS

Lang's Handbook of Chemistry (15$^{th}$ ed.). www.Knovel.com.*
CA:73:87449 abs of JP45017662 Jun. 18, 1970.*
CA:100:104018 abs of JP58140043 Aug. 19, 1983.*
CA:54:22128 abs of Chem Zentr by Matsushita 129 pp 3730 1958.*
CA:87:68861 abs of JP 52023019 Feb. 21, 1977.*

* cited by examiner

Primary Examiner—Jean F. Vollano
(74) Attorney, Agent, or Firm—Roylance, Abrams, Berdo & Goodman, L.L.P.

(57) ABSTRACT

The present invention provides a process for producing a hydroxyalkyl (meth)acrylate which enables to control sufficiently the formation of a diester at the time of a reaction and/or at the time of distillation.

In the process for producing the hydroxyalkyl (meth)acrylate which comprises the step of carrying out a reaction between (meth)acrylic acid and an alkylene oxide in the existence of a catalyst, (1) the reaction between (meth)acrylic acid and the alkylene oxide, or (2) distillation of the resultant hydroxyalkyl (meth)acrylate is performed in the coexistence of a liquid having the relative dielectric constant of not less than 20 at 25° C.

4 Claims, No Drawings

PROCESS FOR PRODUCING HYDROXYALKYL (METH)ACRYLATE

BACKGROUND OF THE INVENTION

A. Technical Field

The present invention relates to a process for producing a hydroxyalkyl (meth)acrylate by performing a reaction between (meth)acrylic acid and an alkylene oxide.

B. Background Art

In the case of producing a hydroxyalkyl (meth)acrylate by performing a reaction between (meth)acrylic acid and an alkylene oxide, the formation of a diester (alkyleneglycol di(meth)acrylate) as a by-product has so far been a problem. The diester has two unsaturated bonds within one molecule, and promotes the polymerization of an object, the hydroxyalkyl (meth)acrylate, and causes the trouble such as clogging of an apparatus. Furthermore, in the case of producing a (co)polymer from a raw material of the hydroxyalkyl (meth) acrylate containing the diester, turbidity arises in the resulting polymer, or the hydroxyalkyl (meth)acrylate containing the diester causes the occurrence of gelation at the time of polymerization. Furthermore, the vapor pressure of the diester is approximate to that of the hydroxyalkyl (meth) acrylate. Therefore, once the diester is formed, the separation thereof is extremely difficult. In addition, when an object, the hydroxyalkyl (meth)acrylate is distilled and purified, the diester is also formed by a disproportionation reaction thereof.

It is known that the diester is apt to form when a reaction liquid of (meth)acrylic acid and the alkylene oxide, or the resulting hydroxyalkyl (meth)acrylate is elevated to a high temperature (e.g. JP-A-133227/1976). Therefore, if a reaction temperature or a distillation temperature is low, the formation of the diester is controlled to some degree. However, when the reaction temperature is low, the period of reaction step time lengthens very much, and so that there is not only a possibility that the productivity falls, but also a possibility that part of a product polymerizes because of the long period of reaction step time or that other by-products increase. Accordingly, falling the reaction temperature or the distillation temperature is not a practical countermeasure.

A method of controlling the formation of the diester at the time of distillation by deactivating a specific catalyst used in the reaction is disclosed (e.g. JP-A-194321/1993). However, there is a disadvantage that the available catalyst is limited, or that the catalyst is not applicable to the formation of the diester at the time of the reaction, and the control effect thereof was insufficient.

SUMMARY OF THE INVENTION

A. Object of the Invention

An object of the present invention is to provide a process for producing a hydroxyalkyl (meth)acrylate which enables to control the formation of a diester sufficiently at the time of reaction and/or at the time of distillation.

B. Disclosure of the Invention

The present inventors diligently studied to achieve the above object. As a result, they have found that the above object could be solved completely by allowing a liquid with a specific relative dielectric constant to coexist at the time of a reaction between (meth)acrylic acid and an alkylene oxide and/or at the time of distillation of a hydroxyalkyl (meth) acrylate.

That is to say, a process for producing a hydroxyalkyl (meth)acrylate, which comprises the step of carrying out a reaction between (meth)acrylic acid and an alkylene oxide in the existence of a catalyst; with the process being characterized in that when the reaction between (meth)acrylic acid and the alkylene oxide is carried out, there coexists a liquid having a relative dielectric constant of not less than 20 at 25° C.

An another process for producing a hydroxyalkyl (meth) acrylate, which comprises the step of carrying out a reaction between (meth)acrylic acid and an alkylene oxide in the existence of a catalyst; with the process being characterized by further comprising the step of distilling the resultant hydroxyalkyl (meth)acrylate in the coexistence of a liquid having a relative dielectric constant of not less than 20 at 25° C.

These and other objects and the advantages of the present invention will be more fully apparent from the following detailed disclosure.

DETAILED DESCRIPTION OF THE INVENTION

First, an outline of a process for producing a hydroxyalkyl (meth)acrylate which the characteristic production process of the present invention can favorably apply to is explained as follows.

First, a reaction between (meth)acrylic acid and an alkylene oxide is carried out in the existence of a catalyst. The reaction rate of this reaction does not reach 100% in many cases, and it is general that the unreacted (meth)acrylic acid or alkylene oxide or such remains in a reaction liquid at the time of the end of the reaction. Then, the above reaction liquid is introduced into the step of removing the unreacted raw materials and such from the reaction liquid. As the subsequent final step, purification such as distillation is performed to obtain an object, the hydroxyalkyl (meth) acrylate.

Hereinafter, the features of the production process of the present invention are explained below.

The alkylene oxide which can be used in the present invention are favorably an alkylene oxide having 2 to 6 carbon atoms, more favorably an alkylene oxide having 2 to 4 carbon atoms. Examples thereof include ethylene oxide, propylene oxide, and butylene oxide, more favorably ethylene oxide and propylene oxide. Incidentally, (meth)acrylic acid used in the present invention means acrylic acid or methacrylic acid.

When the present invention is carried out, the amount of raw materials as charged for the above reaction between the (meth)acrylic acid and the alkylene oxide is favorably in the range of not less than 1 mol of the alkylene oxide per 1 mol of the (meth)acrylic acid, more favorably in the range of 1.0 to 5.0 mol, still more favorably in the range of 1.0 to 3.0 mol, especially favorably in the range of 1.0 to 2.0 mol. In the case where the amount of the alkylene oxide as charged is less than 1.0 mol, it is unfavorable because the reaction rate falls and by-products increase. When the amount of the alkylene oxide as charged is too much, especially more than 5 mol, it is unfavorable economically.

In the present invention, the reaction between the (meth) acrylic acid and the alkylene oxide in the existence of the catalyst can be performed by a method which is conventionally used for this kind of reaction.

In the case where the reaction is performed by a batch method, the reaction is performed by introducing a liquid alkylene oxide into the (meth)acrylic acid. The alkylene oxide may be introduced after the (meth)acrylic acid is dissolved in a solvent. In this case, the alkylene oxide may be added all at once, continuously, or intermittently. In the case of adding the alkylene oxide continuously or intermittently, as is often the case with this kind of reaction, the reaction can be completed by the so-called aging that is carried out by continuing the reaction after introducing the alkylene oxide. Furthermore, it is not always necessary to add the (meth)acrylic acid all at once in the initial stage, and the (meth)acrylic acid can be added after being divided into some portions.

In the case where the reaction is performed by a continuous method, the reaction is performed by adding the (meth) acrylic acid and the liquid alkylene oxide into a reactor such as a tubular or tank reactor continuously and extracting a reaction liquid out of the reactor continuously. In this case, a catalyst may be provided continuously together with raw materials and b e extracted continuously together with the reaction liquid. In the case of using the reactor such as the tubular reactor, a so-called fixed bed manner in which a solid catalyst as packed with the reactor is used may be utilized. In the case of using the reactor such as the tank reactor, the so-called fluidized bed manner in which a solid catalyst as fluidized together with the reaction liquid in the reactor is used may be used. Furthermore, in the cases of these continuous reactions, modes which allow part of the reaction liquid to circulate may be used.

The reaction temperature is usually favorably in the range of 40 to 130° C., more favorably 50 to 100° C. If the reaction temperature is below 40° C., it takes more time for the reaction to proceed and it becomes apart from a practical level. On the other hand, if the reaction temperature is above 130° C., it is unfavorable because by-products become large, or the polymerization of the (meth)acrylic acid of a raw material, the hydroxyalkyl (meth)acrylate of the product and such arise.

Furthermore, this reaction may be performed in a solvent for the purpose of allowing the reaction to proceed mildly or such. As to the solvent, conventional ones such as toluene, xylene, heptane and octane are usable. The pressure in a reaction system during the reaction depends on the kinds or mixing ratios of used raw materials. However, the reaction is usually performed under applied pressure.

In the reaction, conventional polymerization inhibitors are usable. Examples thereof include hydroquinone, hydroquinone monomethyl ether, phenothiazine, copper dibutyldithiocarbamate, or such. The amount of the polymerization inhibitor as added is not especially limited, and is favorably in the range of 0.001 to 1 weight % of a carboxylic acid, more favorably in the range of 0.01 to 0.5 weight %.

In the production process of the present invention, a catalyst used in the reaction between the (meth)acrylic acid and the alkylene oxide is not especially limited, and a catalyst which is used conventionally in this kind of reaction can be used. Examples thereof include iron compounds such as ferric chloride and ferric acetate; chromium compounds such as chromium chloride, chromium acetylacetonate, chromium formate, chromium acrylate, chromium methacrylate, chromium dibutyldithiocarbamate, chromium nitrate, chromium sulfate; amines such as trialkylamines and ion-exchange resins having a quaternary ammonium group. It is favorable to use a basic catalyst such as an amine compound or a basic resin. This basic resin is a high-molecular compound with a basic functional group which is insoluble in a reaction liquid. Examples thereof include tertiary amine compounds, quaternary ammonium salts, cyclic amine compounds such as pyridine, high-molecular compounds with sulfides, favorably basic anion-exchange resins, especially favorably basic anion-exchange resins having an amino group as a basic functional group.

Incidentally, the production process of the present invention enables to reveal the effect of controlling the formation of the diester sufficiently without using a chromium compound with valence number of 6 such as chromic anhydride which has so far exhibited the relatively high effect of controlling the formation of the diester as a catalyst.

In the production process of the present invention, distillation of the product of the hydroxyalkyl (meth)acrylate can be performed according to a method which is conventionally used for this kind of distillation, and for example a distillation apparatus having a portion of a vacant column is enumerated. Furthermore, a thin-film evaporation apparatus may be used in combination.

In the case of using the distillation apparatus with the portion of the vacant column, the so-called distillation column is favorable. The structure thereof can be simple distillation and examples thereof include rectifying columns such as a packed column, a bubble cap tower and a perforated-tray column. Especially, a distillation column comprising plural sieve trays or a distillation column comprising packed materials is favorable. Furthermore, a multiplated perforated-tray column is desirable from a viewpoint of the maintenance of purity or the removal of a polymer. In the method of heating, a method which uses jacket type heaters or a reboiler method which allows bottoms to circulate and performs heating with shell-and-tube heat-exchangers is included. With respect to the pressure condition of distillation, it is favorable to perform distillation under reduced pressure. It is desirable that the operating pressure should be as low as possible from a viewpoint of preventing polymerization, favorably in the range of 0.66 to 40 hPa, more favorably in the range of 1.33 to 13 hPa, still more favorably in the range of 4 to 9.3 hPa. A liquid temperature in the distillation apparatus is usually favorably in the range of 70 to 130° C., more favorably in the range of 80 to 110° C.

The production process according to the present invention is characterized by carrying out the reaction between the (meth)acrylic acid and the alkylene oxide and/or distillation of the resultant hydroxyalkyl (meth)acrylate as explained in the above in the coexistence of a liquid having the relative dielectric constant of not less than 20 at 25° C. This enables to exhibit the effect of controlling the formation of the diester sufficiently on the occasion of the reaction between the (meth)acrylic acid and the alkylene oxide and/or distillation of the hydroxyalkyl (meth)acrylate.

The liquid having the relative dielectric constant of not less than 20 at 25° C. includes water, dimethyl sulfoxide, acetylacetone, acetaldehyde, acetone, acetonitrile, isobutyronitrile, ethanol, ethylene glycol, glycolonitrile, glycerin, o-chlorobenzonitrile, m-chlorobenzonitrile, succinonitrile, o-nitrotoluene, m-nitrotoluene, p-nitrotoluene, 1-nitropropane, 2-nitropropane, nitrobenzene, nitromethane, 1,4-butanediol, furfural, propiononitrile, benzonitrile, formamide, methanol, lactonitrile, and the like, preferably water, dimethyl sulfoxide, acetonitrile, furfural, benzonitrile and formamide, especially preferably at least one member selected from the group consisting of water, dimethyl sulfoxide and acetonitrile. In the case of a liquid having the relative dielectric constant of less than 20 at 25° C., it is difficult to achieve the effect of the present invention, although the liquid is allowed to coexist at the time of the reaction between the (meth) acrylic acid and the alkylene oxide and/or distillation of the hydroxyalkyl (meth)acrylate.

In the case where a liquid having the relative dielectric constant of not less than 20 at 25° C. is coexistent in a reaction liquid, the coexistence ratio of the liquid having the relative dielectric constant of not less than 20 at 25° C. per the reaction liquid is favorably in the range of 0.01 to 70 weight %, more favorably in the range of 0.1 to 50 weight %, especially favorably in the range of 1 to 40 weight %. When the coexistence ratio is less than 0.01 weight %, it is unfavorable because the formation amount of the diester increases, and when the coexistence ratio exceeds 70 weight %, it is unfavorable because the production efficiency deteriorates with the result that the production amount decreases or that it becomes necessary to enlarge production facilities.

Furthermore, in the case where the liquid having the relative dielectric constant of not less than 20 at 25° C. is coexistent in a liquid which is fed to the distillation apparatus, the coexistence ratio of the liquid having the relative dielectric constant of not less than 20 at 25° C. per the liquid which is fed to the distillation apparatus is favorably in the range of 0.01 to 70 weight %, more favorably in the range of 0.1 to 50 weight %, especially favorably in the range of 1 to 40 weight %. When the coexistence ratio is less than 0.01 weight %, it is unfavorable because the formation amount of the diester increases to bring about the deterioration of product quality and the fall of product purity, and when the coexistence ratio exceeds 70 weight %, it is unfavorable because the construction cost of facilities involved in the enlargement of the distillation apparatus increases.

Incidentally, a partial or full catalyst used for the reaction between the (meth)acrylic acid and the alkylene oxide may remain in the liquid which is fed to the distillation apparatus.

In the present invention, a mode that the reaction between the (meth)acrylic acid and the alkylene oxide is performed in the coexistence of the liquid having the relative dielectric constant of not less than 20 at 25° C., or a mode that distillation of the hydroxyalkyl (meth)acrylate is performed in the coexistence of the liquid having the relative dielectric constant of not less than 20 at 25° C. is not especially limited, and examples thereof include (1) a mode that the reaction is performed after adding the liquid having the relative dielectric constant of not less than 20 at 25° C. on the occasion of adding reaction raw materials, (2) a mode that the liquid having the relative dielectric constant of not less than 20 at 25° C. is not coexistent in the reaction and distillation is performed after adding the concerned liquid in distillation, and (3) a mode that the reaction is performed after adding the liquid having the relative dielectric constant of not less than 20 at 25° C. on the occasion of adding reaction raw materials and furthermore distillation is performed in the coexistence of the concerned liquid as it is.

(Effects and Advantages of the Invention)

A process for producing a hydroxyalkyl (meth)acrylate, according to the present invention, enables to control sufficiently the formation of a diester at the time of a reaction and/or at the time of distillation.

DETAILED DESCRIPTION OF THE PREFERRED EMBODIMENTS

Hereinafter, the present invention is more specifically illustrated. However, the present invention is not limited to the below-mentioned examples.

EXAMPLE 1

A 1L-autoclave as equipped with a thermometer, a heating and cooling unit and a stirrer was charged with 480 ml of a water-humidified anion-exchange resin (SA-10; produced by Mitsubishi Chemical Corporation). Furthermore, hydroxyethyl acrylate containing as a polymerization inhibitor phenothiazine and hydroquinone monomethyl ether in a ratio of 0.3 weight % and 0.5 weight % respectively was added thereto so that the liquid volume in the autoclave could be 700 ml, and internal gas of the autoclave was displaced with nitrogen gas after sealing.

20. 1 g/hr. of water having the relative dielectric constant of 78.2 (25° C.), 139.1 g/hr of hydroxyethyl acrylate, 46.3 g/hr of ethylene oxide and 74.5 g/hr of acrylic acid (phenothiazine and hydroquinone monomethyl ether were added in a ratio of 1.1 weight % and 1.9 weight % respectively to the acrylic acid as a polymerization inhibitor) were respectively sent into the autoclave through piping fitted to the autoclave by use of pumps for sending each liquid.

The liquid was extracted out by using a pump so that the liquid level could be kept constant.

The temperature in the autoclave was controlled to keep 85° C., and a reaction was carried out until the composition of the extracted liquid became stable.

The experimental result was that the reaction rate of acrylic acid was 70%, and that the selectivity (on the basis of acrylic acid) of a diester was 0.53 mol/mol %.

Comparative Example 1

A 1L-autoclave as equipped with a thermometer, a heating and cooling unit and a stirrer was charged with 480 ml of a water-humidified anion-exchange resin (SA-10; produced by Mitsubishi Chemical Corporation). Furthermore, hydroxyethyl acrylate containing as a polymerization inhibitor phenothiazine and hydroquinone monomethyl ether in a ratio of 0.3 weight % and 0.5 weight % respectively was added thereto so that a liquid volume in the autoclave could be 700 ml, and internal gas of the autoclave was displaced with nitrogen gas after sealing.

147.3 g/hr of hydroxyethyl acrylate, 58.7 g/hr of ethylene oxide and 78.0 glhr of acrylic acid (phenothiazine and hydroquinone monomethyl ether were added in a ratio of 1.1 weight % and 1.9 weight % respectively to the acrylic acid as a polymerization inhibitor) were respectively sent into the autoclave through piping fitted to the autoclave by use of pumps for sending each liquid.

The liquid was extracted out by using a pump so that the liquid level could be kept constant.

The temperature in the autoclave was controlled to keep 85° C., and a reaction was carried out until the composition of the extracted liquid became stable.

The experimental result was that the reaction rate of acrylic acid was 77.3%, and that the selectivity (on the basis of acrylic acid) of a diester was 1.1 mol/mol %.

Comparative Example 2

A 1L-autoclave as equipped with a thermometer, a heating and cooling unit and a stirrer was charged with 480 ml of a water-humidified anion-exchange resin (SA-10; produced by Mitsubishi Chemical Corporation). Furthermore, hydroxyethyl acrylate containing as a polymerization inhibitor phenothiazine and hydroquinone monomethyl ether in a ratio of 0.3 weight % and 0.5 weight % respectively was added thereto so that a liquid volume in the autoclave could be 700 ml, and internal gas of the autoclave was displaced with nitrogen gas after sealing.

41.5 g/hr of hydroxyethyl acrylate, 14.1 g/hr of ethylene oxide and 23.3 g/hr of acrylic acid (phenothiazine and hydroquinone monomethyl ether were added in a ratio of 1.1 weight % and 1.9 weight % respectively to the acrylic acid as a polymerization inhibitor) were respectively sent into the autoclave through piping fitted to the autoclave by use of pumps for sending each liquid.

The liquid was extracted out by using a pump so that the liquid level could be kept constant.

The temperature in the autoclave was controlled to keep 70° C., and a reaction was carried out until the composition of the extracted liquid became stable.

The experimental result was that the reaction rate of acrylic acid was 71.4%, and that the selectivity (on the basis of acrylic acid) of a diester was 0.85 mol/mol %.

EXAMPLE 2

10 g of hydroxyethyl acrylate and a strong basic anion-exchange resin (SA-10; produced by Mitsubishi Chemical Corporation) were added to a glass screw bottle wherein the anion-exchange resin was in a ratio of 50 volume % per hydroxyethyl acrylate. Furthermore, water (having the relative dielectric constant of 78.2 at 25° C.) or dimethyl sulfoxide (having the relative dielectric constant of 47 at 25° C.) was added thereto wherein the water or dimethyl sulfoxide was in a ratio of 20 volume % per hydroxyethyl acrylate, and the glass screw bottle was dipped into an oil bath of 80° C. for 4 hours with stirring. Thereafter, the increase amount of a diester was measured by gas-chromatography.

The experimental result was that the increase amount of the diester was in a ratio of 0.9 weight % in the case of adding water, and that the increase amount of the diester was in a ratio of 3.1 weight % in the case of adding dimethyl sulfoxide.

Comparative Example 3

The same operation as of Example 2 was performed except that n-decane (having the relative dielectric constant of 2 at 25° C.) or nothing was added instead of water or dimethyl sulfoxide.

The experimental result was that the increase amount of the diester was in a ratio of 10 weight % in the case of adding n-decane, and that the increase amount of the diester was in a ratio of 6.5 weight % in the case of adding nothing.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing a hydroxyalkyl acrylate or hydroxyalkyl methacrylate, which comprises the step of carrying out a reaction between acrylic acid or methacrylic acid, respectively, and an alkylene oxide in the presence of a basic anion-exchange resin catalyst; with the process being characterized in that the reaction between acrylic acid or methacrylic acid and the alkylene oxide is carried out in the presence of a liquid having a dielectric constant of not less than 20 at 25° C., wherein the liquid having a dielectric constant of not less than 20 at 25° C. is selected from the group consisting of water, dimethyl sulfoxide, acetylacetone, acetaldehyde, acetone, acetonitrile, isobutyronitrile, ethanol, glycolonitrile, o-chlorobenzonitrile, m-chlorobenzonitrile, succinonitrile, o-nitrotoluene, m-nitrotoluene, p-nitrotoluene, nitrobenzene, furfural, propiononitrile, benzonitrile, formamide, methanol, and lactonitrile.

2. A process for producing a hydroxyalkyl acrylate or hydroxyalkyl methacrylate, which comprises the step of carrying out a reaction between acrylic acid or methacrylic acid, respectively, and an alkylene oxide in the presence of a catalyst; with the process being characterized by further comprising the step of distilling the resultant hydroxyalkyl acrylate or hydroxyalkyl methacrylate in the presence of a liquid having a dielectric constant of not less than 20 at 25° C., wherein the liquid having a dielectric constant of not less than 20 at 25° C. is selected from the group consisting of dimethyl sulfoxide, acetylacetone, acetaldehyde, acetone, acetonitrile, isobutyronitrile, ethanol, glycolonitrile, o-chlorobenzonitrile, m-chlorobenzonitrile, succinonitrile, o-nitrotoluene, m-nitrotoluene, p-nitrotoluene, nitrobenzene, furfural, propiononitrile, benzonitrile, formamide, methanol, and lactonitrile.

3. A process according to claim 1, wherein the liquid having a dielectric constant of not less than 20 at 25° C. is selected from the group consisting of water, dimethyl sulfoxide, and acetonitrile.

4. A process according to claim 2, wherein the liquid having a dielectric constant of not less than 20 at 25° C. is selected from the group consisting of dimethyl sulfoxide, and acetonitrile.

* * * * *